US00PP12816P2

(12) United States Plant Patent
Lyrene

(10) Patent No.: US PP12,816 P2
(45) Date of Patent: Jul. 30, 2002

(54) BLUEBERRY PLANT CALLED 'MILLENNIA'

(75) Inventor: Paul M. Lyrene, Gainesville, FL (US)

(73) Assignees: Thomas D. Stadsklev; Florida Foundation Seed Producers, Inc., both of Greenwood, FL (US)

( * ) Notice: Subject to any disclaimer, the term of this patent is extended or adjusted under 35 U.S.C. 154(b) by 0 days.

(21) Appl. No.: 09/684,690

(22) Filed: Oct. 10, 2000

(51) Int. Cl.[7] ..... A01H 5/00
(52) U.S. Cl. ..... Plt./157
(58) Field of Search ..... Plt./157, 156

*Primary Examiner*—Bruce R. Campell
*Assistant Examiner*—June Hwu

(57) ABSTRACT

A new and distinct low-chill tetraploid highbush blueberry (Vaccinium) variety of complex hybrid ancestry, based largely on *V. corymbosum* L. with some genes from *V. darrowi*. Because of its interspecific hybrid origin, 'Millennia' does not correspond exactly to any botanical species, but is closest to *Vaccinium corymbosum*. It belongs to the commercial class of blueberry called "southern highbush". Its novelty consists of the following unique combination of features:

1. Produces a vigorous bush that is upright but somewhat spreading.
2. Has high resistance to cane canker (*Botryosphaeria corticis*), medium resistance to phytophthora root rot (*Phytophthora cinnamomi*), and low to medium resistance to stem blight (*Botryosphaeria dothidia*).
3. Flowers and fruits well in areas of central and north Florida where the mean temperature of the coldest month is 57° F. or colder.
4. Ripens its fruit 60 days after flowering in north-central Florida (latitude 29.5).
5. Ripens 80% of its fruit between April 15 and May 10 in north-central Florida.
6. Produces berries that are large, firm, light blue in color, have a good picking scar, and a mild, pleasant, flavor.
7. Propagates readily from softwood cuttings.

4 Drawing Sheets

ORIGIN OF THE VARIETY

'Millennia' was a seedling from the cross 'FL85-69'× 'O'Neal', made in 1986 in a greenhouse in Gainesville, Fla. Neither parent is patented. 'FL85-69' was an advanced selection from the Florida blueberry-breeding program and 'O'Neal' is a cultivar released from North Carolina State University in 1987. 'Millennia' was selected from a high-density field nursrey based on fruit and plant characteristics in 1988. The plant was dug in December 1988, potted, chilled in a cooler, and hand-pollinated in a greenhouse in March 1989. Based on the extremely high fruit quality and large fruit size in the greenhouse, the plant was propagated by cuttings and was planted in an 8-plant plot at the Horticultural Research Unit in Gainesville, Fla. in January 1991. At the same time, a 10-plant pot was planted on a commercial blueberry farm in Windsor, Fla. Because the clone gave high yields of early-ripening, large berries, 1000 more 'Millennia' plants were propagated and planted at Windsor in January 1998. Based on high yields, high fruit quality, and early ripening in these plots, the cultivar was selected for release as a cultivar after the fruiting season of 1999. 'Millennia' differs from its parent 'FL85-69' in having a berry that is larger and lighter blue in color, with a smaller picking scar and higher firmness. 'Millennia' differs from its parent 'O'Neal' by having a lower chilling requirement, a berry that is much lighter blue in color, a more spreading bush habit, and a higher yield.

ASEXUAL PROPAGATION OF THE VARIETY

'Millennia' has been propagated by rooting softwood cuttings under mist on numerous occasions in Gainesville, Fla. (Alachua County). In every case, all resulting plants have displayed the characteristics of the variety.

DESCRIPTION OF THE VARIETY

Figure 1:
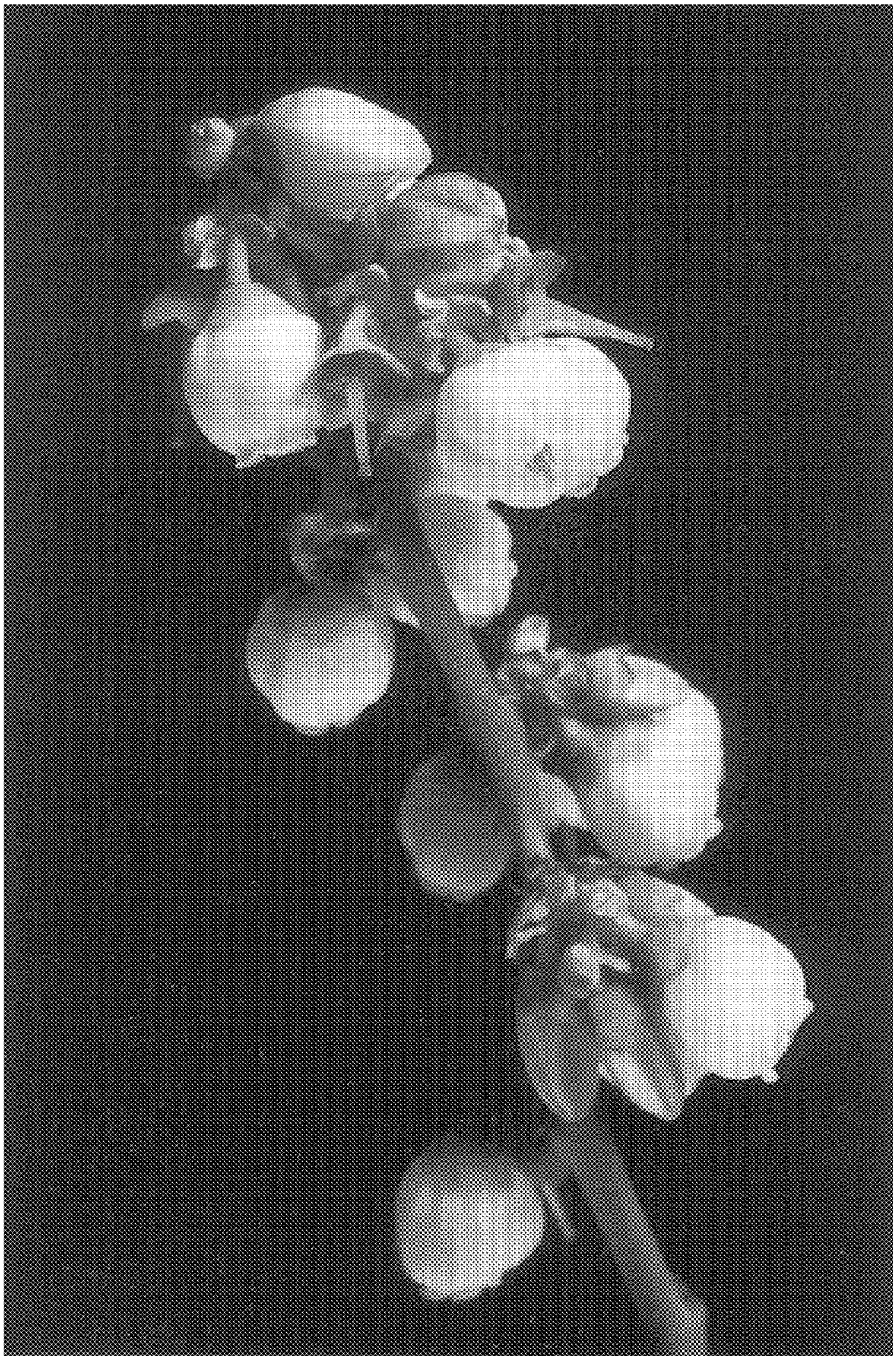
FIG. 1 illustrates a flowering branch of 'Millennia', showing the arrangement of the flowers in the cluster, the shape of the corolla, and the pistil after the flower has been pollinated and the corolla has abscised.
Figure 2:
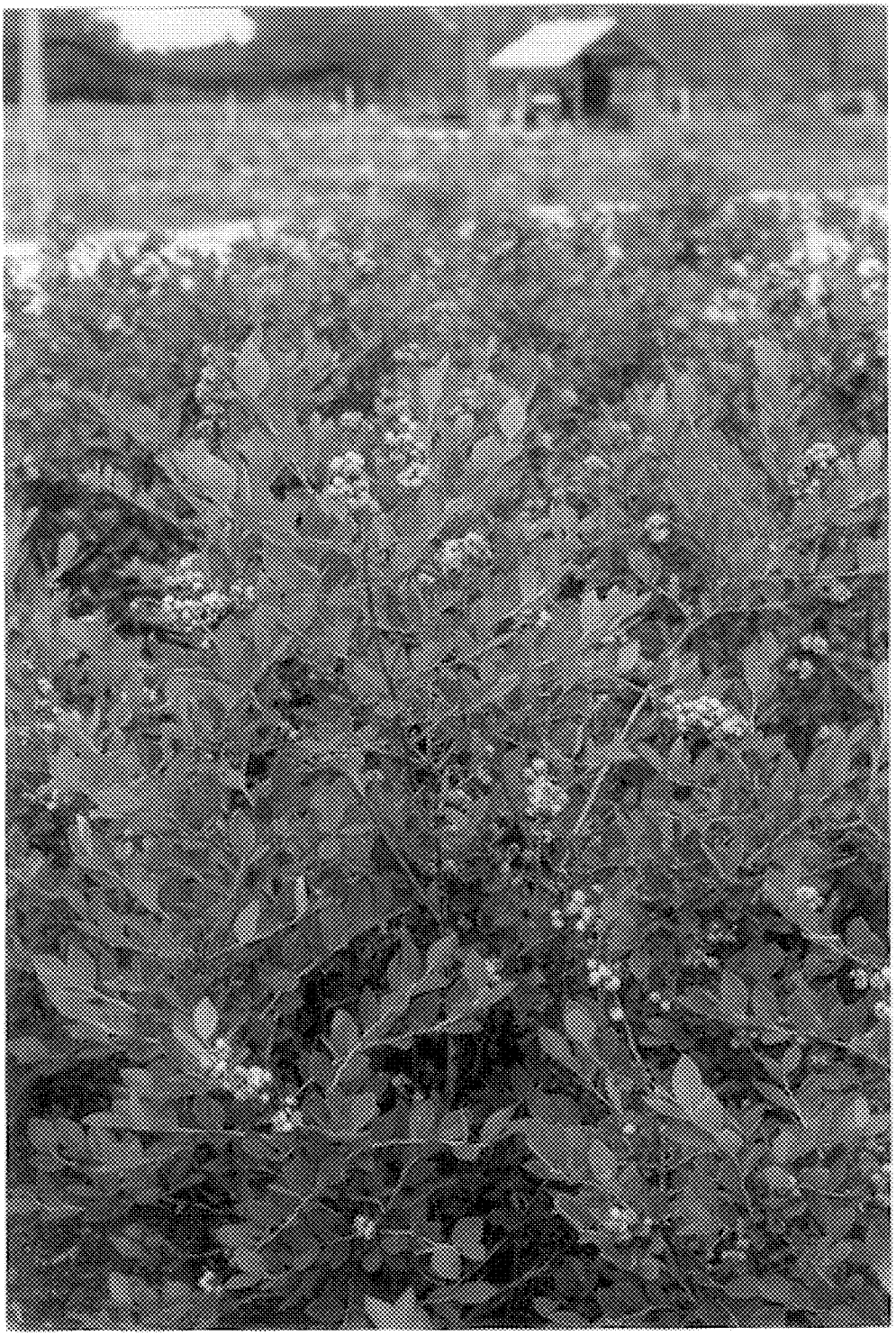
FIG. 2 shows 2-year-old plants of 'Millennia' growing in pine bark in a field in north Florida at the end of April 2000. Ripe and unripe berries and new shoots are shown.
Figure 3:
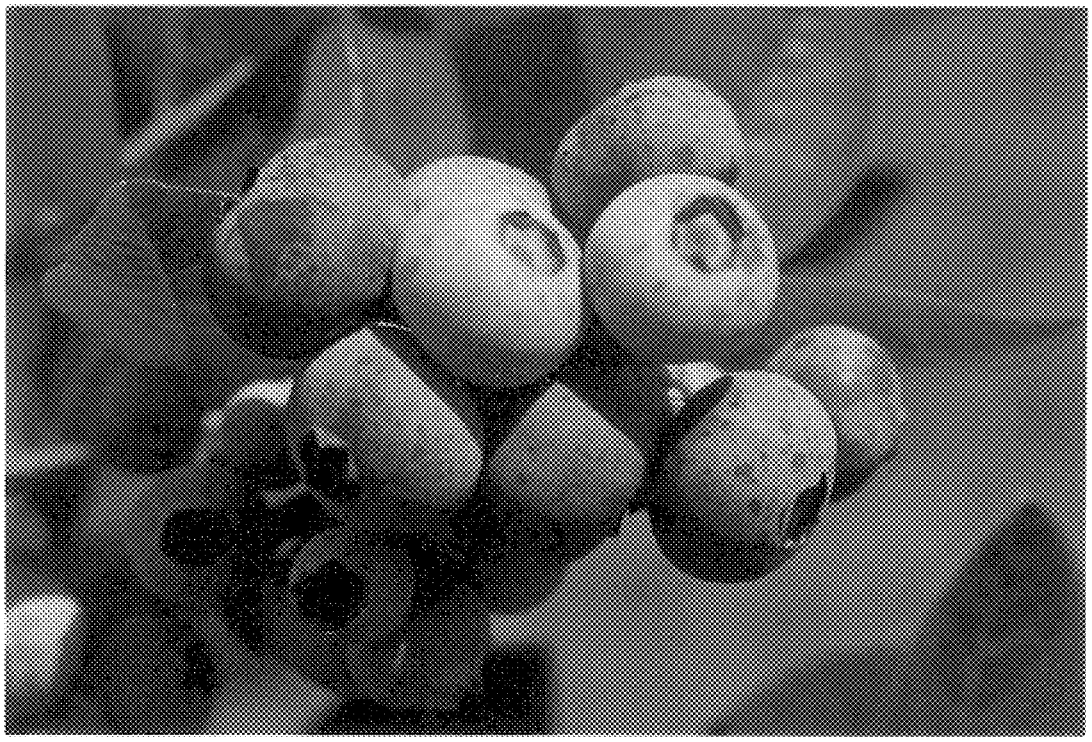
FIG. 3 shows ripe and unripe berries clustered on the stem. The relatively undeveloped calyx lobes and the wide calyx aperture are illustrated.
Figure 4:
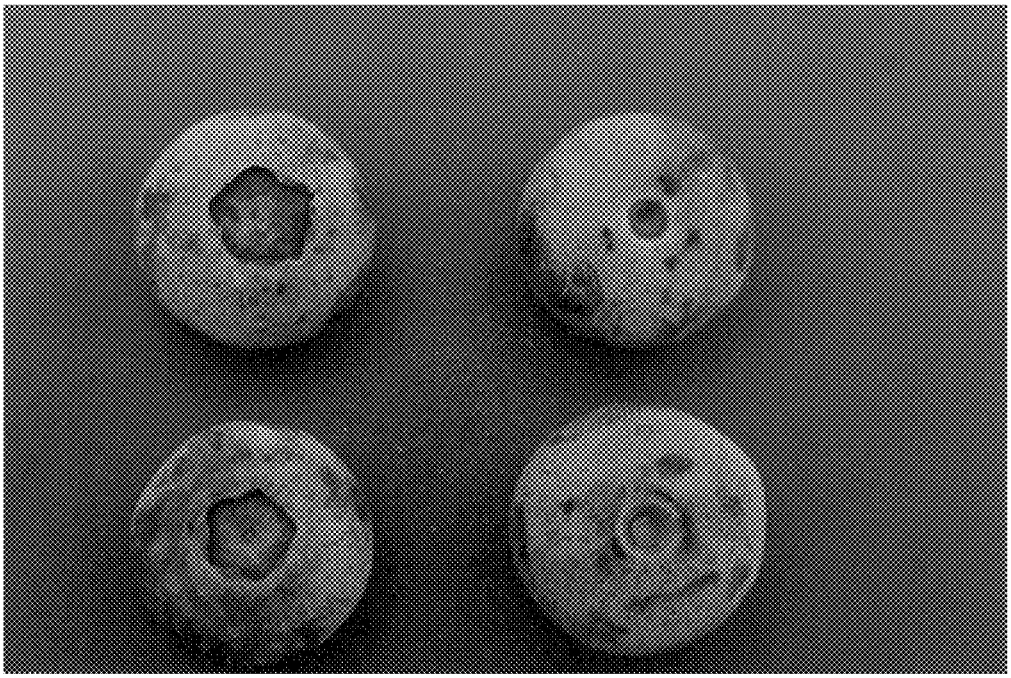
FIG. 4 shows ripe berries in two aspects. The wide calyx aperture is shown for two berries and the small picking scar is shown for two.

The following is a detailed botanical description of 'Millennia', its flowers, fruit and foliage, based on observation of specimens grown in the field in Windsor, near Gainesville, Fla. Color descriptions, except those given in common terms, use terminology from "The Pantone Book of Color" by Leatrice Eiseman and Lawrence Herbert; Harry N. Abrams, Inc. Publishers, New York. Due to limitations of in film, the colors in the drawings do not always exactly match the colors in the plant. In cases where the colors in the drawings differ from those indicated by the Pantone color codes, the Pantone should be considered the more accurate of the two.

Bush: Bush size is reported for plants that had been growing for two years in a bed of pine bark in a field in Windsor, Fla. The bed had been initiated using rooted cuttings that were 6 inches tall at the time they were planted. The bed was provided with overhead irrigation and was managed like a commercial blueberry planting in Florida.

*Plant height.*—120 cm.

*Canopy diameter.*—115 cm.

*Plant vigor compared to other Florida southern highbush cultivars.*—High.

*Growth habit.*—Between upright and spreading.

*Flower bud number compared to other Florida cultivars.*—High to very high.

*Cold hardiness.*—Except for the flowers and fruit, some of which have been killed in some years by freezes in February and March, 'Millennia' has not suffered freeze damage to the bush in Gainesville. Dormant plants have withstood temperatures of 18° F. without damage.

*Chilling requirement.*—Based on the time and extent of spring vegetative growth and flower bud break in Gainesville, 'Millennia' appears to have a chilling requirement of about 350 hours below 45° F. after the plants have become dormant in the winter.

*Productivity.*—Large plants on good soil have yielded 5 to 6 pounds per plant per year after 3 to 4 years in the field.

*Suckering tendency.*—Medium to high, with 5–10 major canes from the base of 2-year-old plants. Texture of 2-year-old main canes: medium rough.

*Color of 2-year-old rough bark.*—"Cameo Rose", Pantone 14-1310.

Twigs:

*Color of smooth shoots from previous year's spring flushes, viewed Mar. 2, 2000.*—"Cedar Wood", Pantone 17-1525.

*Color of smooth shoots from previous year's late-summer flushes, viewed Mar. 2, 2000.*—"Fall Leaf", Pantone 15-1132.

*Internode length.*—1.1 cm on strong upright shoots.

Characteristics of mature leaves:

*Leaf length excluding petiole.*—Typically 60 to 65 mm, but can be 80 mm or longer on vigorous shoots.

*Leaf width.*—Typically 30 to 35 mm but can be 40 mm or wider on vigorous shoots.

*Leaf shape.*—Oval.

*Leaf tip.*—Acuminate to mucronate.

*Leaf margin.*—Minutely serrate, with small, round, sessile glands located along the margin of the leaf at points where the margin is indented.

*Color of upper surface.*—A shade of green called "Peridot", Pantone 17-0336.

*Color of lower surface.*—A shade of green called "Peridot", Pantone 17-0336.

*Pubescence, lower leaf surface.*—Essentially glabrous.

*Pubescence, leaf margins.*—Glabrous.

*Synchrony of leafing and flowering.*—Plants usually flower before they leaf in north Florida.

Flowers:

*Fragrance.*—Light to medium lilac fragrance.

*Flower cluster: (tight, medium, or open).*—Medium.

*Average number of flowers per cluster.*—4–7, mostly 4–5.

*Inflorescence.*—Pedicel length: 4 mm.

*Peduncle length.*—5 mm.

*Corolla length from pedicel attachment point to the corolla tip.*—10.9 mm.

*Diameter of corolla tube at widest point.*—9.2 mm.

*Corolla aperture diameter.*—4.0 mm.

*Corolla color.*—Normally "White Swan", Pantone 12-0000, but night temperatures below 7° C. during the week before the flowers open can introduce varying amounts of pink to the corolla color, particularly to the upper parts of the corolla that are exposed to the most intense sunlight. The most intensely pigmented parts of the corolla range between 'White Swan' and 'Seashell Pink', Pantone 13-1409, if night temperatures in the field are near freezing and the days are bright and sunny before and during the time the flowers open.

*Stamens and pistils.*—Typical for highbush blueberry.

*Pollen abundance.*—Abundant.

*Pollen staining with acetocarmine dye.*—87% of the grains stain. This indicates somewhat below-normal male fertility.

*Color of dried pollen.*—"Straw", Pantone 13-0902.

*Average date by which the first 50% of the flowers have opened in Gainesville, Fla.*—February 16.

*Self-compatibility.*—Highly self-incompatible and self-unfruitful; in one test, 100 flowers hand self-pollinated in a greenhouse produced only 2 small, seedless berries; in a second test, 130 self-pollinated flowers produced no berries.

Berry:

*Weight.*—Leader berries on young plants: 2.37 g per berry.

*Calyx lobes on mature berry, size and shape.*—Very small, almost nonexistent.

*Berry height.*—12 mm.

*Berry width.*—18 mm.

*Berry surface color, ripe on the plant.*—"Ashes of Roses", Pantone 15-0703.

*Berry surface color with wax removed.*—"Slate Black", Pantone 19-0814.

*Color of the interior berry flesh in a ripe berry.*—"Frozen Dew", Pantone 13-0513.

*Color of washed, dried seeds.*—"Sierra", Pantone 18-1239 (a shade of brown).

*Surface wax.*—Above-normal resistance to rubbing off compared to other southern highbush cultivars.

*Berry resistance to cracking.*—Above average for southern highbush blueberry cultivars, but some berries will crack if continuously wet for more than 36 hours after they are ripe.

*Pedicel scar.*—Small and dry.

*Berry firmness.*—High.

*Berry flavor.*—Sweet, sub acid.

*Berry fragrance.*—None.

*Berry texture.*—Good; thin skins, small seeds, and inconspicuous sclereids.

*Maturity.*—Date when the first 50% of the crop is ripe on 'Millennia' averages April 28 in Gainesville compared to April 27 for 'Star' (U.S. Plant Pat. No. 10,675) and May 1 for 'Sharpblue' (unpatented).

*Intended market class.*—Principally intended for the early-season fresh market. The berries can also be marketed as a frozen product, but market prices are normally higher for the fresh berries due to the early season of ripening.

Diseases, insects, and mites:

*Cane canker resistance.*—Highly resistant.

*Dieback due to stem blight.*—Moderately susceptible.

*Phytophthora root rot.*—Moderately resistant.

*Fungal leaf spots.*—Above-average resistance.

*Blueberry bud mites.*—Resistant.

Ease of propagation: Roots readily from softwood cuttings.

I claim:

1. A new and distinct highbush blueberry plant, substantially as illustrated and described, characterized by its semi-upright bush, low chill requirement, large, high-quality fruit and blue fruit color that is lighter than normal for highbush blueberry.

* * * * *